(12) United States Patent
Jacobson et al.

(10) Patent No.: US 10,758,503 B2
(45) Date of Patent: ***Sep. 1, 2020

(54) COMPOSITION CONTAINING GLIBENCLAMIDE

(71) Applicant: BIOGEN CHESAPEAKE LLC, Cambridge, MA (US)

(72) Inventors: Sven Martin Jacobson, New York, NY (US); Robert Ang, Cupertino, CA (US)

(73) Assignee: Biogen Chesapeake LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/599,327

(22) Filed: Oct. 11, 2019

(65) Prior Publication Data

US 2020/0093767 A1    Mar. 26, 2020

Related U.S. Application Data

(60) Continuation of application No. 15/989,738, filed on May 25, 2018, now Pat. No. 10,441,556, which is a division of application No. 13/779,511, filed on Feb. 27, 2013, now Pat. No. 10,004,703, which is a continuation of application No. 12/444,908, filed as application No. PCT/US2007/081128 on Oct. 11, 2007, now abandoned.

(60) Provisional application No. 60/851,412, filed on Oct. 12, 2006.

(51) Int. Cl.
| | |
|---|---|
| *A61K 31/155* | (2006.01) |
| *A61K 31/18* | (2006.01) |
| *A61K 31/175* | (2006.01) |
| *A61K 31/64* | (2006.01) |
| *A61K 45/06* | (2006.01) |

(52) U.S. Cl.
CPC ............ *A61K 31/18* (2013.01); *A61K 31/155* (2013.01); *A61K 31/175* (2013.01); *A61K 31/64* (2013.01); *A61K 45/06* (2013.01)

(58) Field of Classification Search
None
See application file for complete search history.

(56) References Cited

U.S. PATENT DOCUMENTS

| | | |
|---|---|---|
| 5,192,753 A | 3/1993 | McGeer |
| 5,258,185 A | 11/1993 | Bauer |
| 5,817,623 A | 10/1998 | Ishii |
| 5,856,360 A | 1/1999 | Salzman |
| 5,977,109 A | 11/1999 | Nkakura |
| 6,537,578 B1 | 3/2003 | Bhagwat et al. |
| 10,441,556 B2 * | 10/2019 | Jacobson ............... A61K 31/64 |
| 2003/0125338 A1 | 7/2003 | Connop et al. |
| 2003/0215889 A1 | 11/2003 | Simard |
| 2006/0100183 A1 | 5/2006 | Simard |
| 2006/0183803 A1 | 8/2006 | Hevia et al. |
| 2006/0189663 A1 | 8/2006 | Holm |
| 2006/0276411 A1 | 12/2006 | Simard et al. |
| 2007/0249583 A1 | 10/2007 | Stein et al. |
| 2008/0220441 A1 | 9/2008 | Birnbaum |
| 2009/0233995 A1 | 9/2009 | Lautt |

OTHER PUBLICATIONS

Ryan et al., "Improving Metabolic Control Leads to Better Working Memory in Adults with Type 2 Diabetes", Diabetes Care, vol. 29, No. 2, Feb. 2006, pp. 345-351.
Rudinger, In Peptide Hormones, J.A. Parsons, ed., University Park Press, Baltimore, 1976, pp. 1-7.
Butterfield et al., "Elevated risk of type 2 diabetes for development of Alzheimer disease", 1842 Biochimica et Biophysica Acta 1693-1706, 2014.
Baraka et al. "Study of the effect of inhibiting galanin in Alzheimer's disease induced in rats", European Journal of Pharmacology, 641 (2-3): 123-7 (Sep. 1, 2010).

* cited by examiner

*Primary Examiner* — John D Ulm
(74) *Attorney, Agent, or Firm* — Rothwell, Figg, Ernst & Manbeck, P.C.

(57) ABSTRACT

NSC antagonists are disclosed as useful in the treatment of dementia, in delaying the onset of dementia, and in the prevention of dementia. Dementia so treated may be, for example, Alzheimer's Disease (AD). NSC antagonists for treating dementia such as AD may be administered alone, a) in combination with other drugs used for treating dementia, b) in combination with drugs that stabilize or increase blood plasma glucose levels, or with both a) and b). Pharmaceutical compositions, dosage forms, and methods for using the same are disclosed, which include NSC antagonists, NSC antagonists combined with dementia drugs, NSC antagonists combined with glucose-level stabilizing or enhancing drugs, or combinations of these. Dosage forms may be designed to provide stable plasma levels for extended periods of time. Exemplary pharmaceutical compositions include compositions including glibenclamide and memantine; glibenclamide and donepezil; tolbutamide and memantine; tolbutamide and donepezil; and these compositions further including glucagon and/or glucose.

20 Claims, No Drawings

COMPOSITION CONTAINING GLIBENCLAMIDE

BACKGROUND

This application is a continuation of U.S. Ser. No. 15/989,738 filed May 25, 2018, which is a divisional of U.S. Ser. No. 13/779,511 filed Feb. 27, 2013, now U.S. Pat. No. 10,004,703, which is a continuation of U.S. Ser. No. 12/444,908, filed Apr. 9, 2009, now abandoned, which is a national phase application claiming priority under 35 U.S.C. § 120 from PCT/USN/081128 filed on Oct. 11, 2007, and claims the benefit, under 35 U.S.C. § 119(e), of U.S. Provisional Application 60/851,412 filed Oct. 12, 2006 , the entire disclosures of which applications are hereby incorporated by reference in their entireties.

Sulfonylurea drugs and related drugs are believed to act on the type 1 sulfonylurea receptor (SUR1 receptor) and the type 2 sulfonylurea receptor (SUR2). Sulfonylurea drugs have been shown to be effective in treating stroke and spinal cord injury due to the drug acting on a non selective cation channel which has type 1 sulfonylurea receptor (SUR1) binding sites and thus binds to Sulfonylureas. This channel is a non-selective $Ca^{++}$-activated ATP-sensitive cation channel termed the "$NC_{Ca-ATP}$ channel" (see, e.g., Chen and Simard, Journal of Neuroscience 21:6512-6521 (2001); and Chen et al., Journal of Neuroscience 23; 8568-8577 (2003), each hereby incorporated by reference) and is believed to include a regulatory sub-unit including a SUR1 receptor, and a pore subunit that has similar properties to, and may be comprised of, a TRPM4 channel (see, e.g., Simard et al., Biochimica et Biophysica Acta, 1772(8):947-957 (2007), hereby incorporated by reference). There is also some ex-vivo evidence that certain Sulfonylureas may have an effect in treating Parkinson's disease, and the $K_{ATP}$ channel has been implicated in this regard.

There have been numerous studies as to the association between Alzheimer's disease (AD) and Type 2 Diabetes. Type 2 Diabetes has been found to be both negatively and positively associated with AD. Thus, according to the scientific literature, the relationship, if any, between Type 2 Diabetes and AD remains unknown.

Dementia is a term describing loss of mental function in a patient. As used herein, the term "dementia" refers to broadly to a psychiatric or medical condition characterized by cognitive deficits that may include impairments in memory, reasoning, planning, and judgment. Senile dementia is a dementia having an onset at an advanced age. One form of dementia that is more frequent in aged than in younger individuals is multi-infarct dementia, characterized by brain damage resulting from multiple infarcts, or strokes. Other forms of brain injury, brain trauma, inflammation, or other insult to the brain may lead to or exacerbate dementia. Another form of dementia, Alzheimer's Disease (AD), is a particularly prevalent form of dementia, and is more frequently found in aged than in younger individuals.

AD is the most common form of dementia among older people, and initially involves the parts of the brain that control thought, memory, and language. There are classic histolopathologic findings in AD such as neurofibrillary tangles, neuritic (senile) plaques, Hirano bodies, granulovacuolar bodies of Simchowicz, Pick bodies and Lewy bodies. Many of these histopathologic findings are associated with neuronal cell death which occurs insidiously many years before symptoms manifest.

SUMMARY

Applicants disclose herein the use of sulfonylurea receptor antagonists and of blockers of non-selective channels (the $NC_{Ca-ATP}$ channel, the TRPM4 channel, and the TRPM5 channel) to treat dementia. The use of Sulfonylureas, active metabolites of Sulfonylureas, Sulfonylurea mimetics, or any drug or chemical compound effective to antagonize a sulfonylurea receptor 1 (SUR1 receptor) or to block or reduce the physiological activity of channels associated with SUR1 receptors, for ameliorating dementia, for ameliorating the effects of dementia, for treating dementia, for reducing the effects of dementia, or for preventing or delaying the onset of dementia is disclosed herein. Sulfonylureas, Sulfonylurea mimetics, or any drug or chemical compound selective for SUR1 receptors that antagonize SUR1 receptors, or are effective to block or reduce the physiological activity of channels associated with SUR1 receptors, including antagonists and blockers of the $NC_{Ca-ATP}$ channel and antagonists and blockers of the TRPM4 channel and the TRPM5 channel, are collectively termed herein "NSC antagonists" referring to the common action of antagonizing the activity of the non-selective channels the $NC_{Ca-ATP}$ channel (regulated by SUR1 receptors) and the TRPM4 channel and the TRPM5 channel. A particular form of dementia treated by the methods, compositions, and formulations disclosed herein is Alzheimer's Disease (AD).

Thus, the use of NSC antagonists for treating AD, reducing the effects of AD, or delaying or preventing the onset of AD is disclosed herein. Thus, methods, pharmaceutical compositions and formulations for the treatment, palliation, amelioration, slowing the progression of, or prevention of AD are disclosed herein.

Embodiments of the invention disclosed herein include the use of a NSC antagonist in the manufacture of a medicament for the treatment of dementia, including wherein the dementia is Alzheimer's Disease (AD). For example, a NSC antagonist for use in the manufacture of a medicament for the treatment of dementia, may be selected from glibenciamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, SKF 9635, and combinations thereof.

In embodiments of the invention disclosed herein, a NSC antagonist is used together with an other compound in the manufacture of a medicament for the treatment of dementia, such as, e.g., AD, wherein the other compound is a compound used in the treatment of dementia. For example, an other compound used in the treatment of dementia may be selected from memantine, donepezil, galantamine, rivastigmine, tacrine, and combinations thereof.

In further embodiments of the invention disclosed herein, the NSC antagonist used in the manufacture of a medicament for the treatment of dementia, such as, e.g., AD, may comprises a combination of compounds comprising a) at least one compound selected from: glibenclamide, 4-trans-hydroxy-glibenclamide, 3-cis-hydroxy-glibenclamide, tolbutamide, chlorpropamide, tolazamide, repaglinide, nateglinide, meglitinide, tolazamide, gliquidone, LY397364, LY389382, glyclazide, glimepiride, estrogen, estradiol, estrone, estriol, genistein, diethystilbestrol, coumestrol, zearalenone, non-steroidal estrogens, and phytoestrogens; and b) at least one compound selected from: pinkolant, flufenamic acid, mefanamic acid, niflumic acid, rirnonabant, SKF 9635.

In yet further embodiments, the NSC antagonist used in the manufacture of medicaments having features of the invention is selected from: glibenclarnide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, and glimepiride. In still further embodiments, the NSC antagonist used in the manufacture of medicaments having features of the invention is glibenclarnide. In yet further embodiments, the NSC antagonist used in the manufacture of medicaments having features of the invention is selected from pinkolant, flufenamic acid, mefanamic acid, nifumic acid, rimonabant, and SKF 9635. In a further embodiment, the NSC antagonist used in the manufacture of medicaments having features of the invention is pinkolant.

Further embodiments of the invention disclosed herein include a pharmaceutical composition comprising a NSC antagonist; an other compound used in the treatment of dementia; and a pharmaceutically acceptable carrier. For example, a NSC antagonist suitable for such a pharmaceutical composition may be selected from glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, SKF 9635, and combinations thereof. For example, an other compound used in the treatment of dementia suitable for inclusion in a such pharmaceutical composition may be selected from memantine, donepezil, galantamine, rivastigmine, tacrine, and combinations thereof.

Further embodiments of pharmaceutical compositions having features of the invention include pharmaceutical compositions comprising glibenclamide; a compound selected from memantine, donepezil, galantamine, rivastigmine, tacrine, and combinations thereof; and a pharmaceutically acceptable carrier. In further embodiments, a pharmaceutical composition comprises tolbutamide; a compound selected from memantine, donepezil, galantamine, rivastigmine, tacrine, and combinations thereof; and a pharmaceutically acceptable carrier. In yet further embodiments, a pharmaceutical composition comprises chlorpropamide; a compound selected from memantine, donepezil, galantamine, rivastigmine, tacrine, and combinations thereof; and a pharmaceutically acceptable carrier.

In further embodiments, the pharmaceutical compositions having features of the invention include pharmaceutical compositions wherein the NSC antagonist comprises a combination of compounds comprising a) at least one compound selected from: glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, dietlaystilbestrol, coumestrol, zearalenone, non-steroidal estrogens, and phytoestrogens; and b) at least one compound selected from: pinkolant, flufenamic acid, mefanamic acid, niflumic acid, rimonabant, SKF 9635.

In still further embodiments, a pharmaceutical composition may comprise a pharmaceutical composition of any of the above, and further comprising a compound effective to increase blood plasma glucose levels; for example, a compound effective to increase blood plasma glucose levels may be selected from glucose and glucagon.

Embodiments of the invention disclosed herein include pharmaceutical dosage forms comprising any of the above-described pharmaceutical compositions. For example, a pharmaceutical dosage form having features of the invention may be selected from a pill, a tablet, an oral formulation, an intravenous formulation, an intra-arterial formulation, an intramuscular formulation, a subcutaneous formulation, a peritoneal formulation, an inhalational formulation, a rectal formulation, a vaginal formulation, a topical formulation, a gel, an ointment, and a transdermal patch.

In embodiments, a pharmaceutical dosage form having features of the invention includes a pharmaceutical dosage form wherein the NSC antagonist comprises a combination of compounds comprising a) at least one compound selected from: glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, and phytoestrogens; and b) at least one compound selected from: pinkolant, flufenamic acid, rnefunamic acid, niflumic acid, rimonabant, SKF 9635.

Also disclosed herein is a method of treating dementia, such as, e.g., comprising administering a NSC antagonist to a patient in need of such treatment. As disclosed herein, a method of treating dementia, such as, e.g., AD, may include administering a NSC antagonist and an other compound used in the treatment of dementia, to a patient in need of such treatment. A NSC antagonist suitable for the practice of the method disclosed herein may be, for example, selected from glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenaniic acid, mefanamic acid, niflumic acid, rimonabant, SKF 9635, and combinations thereof. An other compound used in the treatment of dementia, such as, e.g., AD, may be selected from memantine, donepezil, galantamine, rivastigmine, tacrine, and combinations thereof.

Also disclosed herein is a method of preventing or delaying the onset of dementia, such as, e.g., AD, comprising administering a NSC antagonist to a patient in need of such treatment. In embodiments, a method of preventing or delaying the onset of dementia, such as, e.g., AD, may comprise administering a NSC antagonist and an other compound used in the treatment of dementia, to a patient in need of such treatment. For example, a NSC antagonist suitable for the practice of such methods may be selected from glibenclamide, 4-trans-hydroxy-glibenclamide, 3-cis-hydroxy-glibenclarnide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, SKF 9635, and combinations thereof. For example, an other compound used in the treatment of dementia, such as , e.g., AD, may be selected from memantine, donepezil, galantamine, rivastigrnine, tacrine, and combinations thereof.

In still further embodiments, a method of preventing or delaying the onset of dementia, such as, e.g., AD, may further comprise administration of a compound effective to increase blood plasma glucose levels; a compound effective to increase blood plasma glucose levels may be, for example, selected from glucose and glucagon.

In embodiments of the methods disclosed herein, the NSC antagonist comprises a combination of compounds comprising a) at least one compound selected from: glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, and phytoestrogens; and b) at least one compound selected from: pinkolant, flufenamic acid, mefanamic acid, niflumic acid, rimonabant, SKF 9635.

Also disclosed herein are kits, including a kit comprising a pharmaceutically acceptable formulation of a NSC antagonist, and a pharmaceutically acceptable formulation of an AD drug; and a kit comprising a pharmaceutically acceptable formulation of a NSC antagonist, a pharmaceutically acceptable formulation of an AD drug, and a pharmaceutically acceptable formulation of a compound effective to increase blood plasma glucose levels.

DETAILED DESCRIPTION

The term "Sulfonylureas" as used in the following disclosure includes Sulfonylureas, Sulfonylurea mimetics, and any other drug or chemical compound that is effective to block or reduce the activity of channels associated with SUR1. In embodiments, the channels associated with SUR1 include the $NC_{Ca-ATP}$ channel (see, e.g., U.S. Patent Application Publications 20030215889, "Non-selective cation channel in neural cells and methods for treating brain swelling"; 20050181980, "Novel non-selective cation channel in neural cells and method for treating brain swelling"; 20060100183, "Therapeutic agents targeting the $NC_{ca-ATP}$ channel and methods of use thereof"; and 20060276411. "Novel non-selective cation channel in neuronal cells and methods for treating brain swelling" all of which applications are hereby incorporated by reference in their entireties) and $K_{ATP}$ channels. In embodiments of the invention, the Sulfonylureas, sulfonylurea mimetics, or other drugs are NSC antagonists effective to block the channels associated with SUR1. In embodiments of the invention, the blockade of the channels associated with SUR1 by NSC antagonists is effective to reduce the amount of neuronal cell death associated with dementia, such as AD. In embodiments of the invention, the blockade of the channels associated with SUR1 by NSC antagonists is effective to prevent neuronal from occurring, delay, or ameliorate cell death associated with dementia, such as AD.

The channels known as the "TRPM4 channel" and as the "TRPM5 channel" are non-selective channels sharing many of the characteristics of the $NC_{Ca-ATP}$ channel, and are postulated by some to be the pore-forming subunit of the SUR1-regulated $NC_{Ca-ATP}$ channel (see, e.g., Simard et al., Biochimica et Biophysica Acta, 1772(8):947-957 (2007)). Blockers of the TRPM4 channel include pinkolant ((R,S)-(3,4-dihydro-6,7-dimethoxy-isoquinoline-1-yl)-2-phenyl-N, N-di[2-(2,3,4-trimethoxyphenyl)ethyl]-acetamide)); fenamates, including flufenamic acid, mefanamic acid, and niflumic acid; rimonabant (SR141716A; (5-(4-Chlorophenyl)-1-(2,4-dichloro-phenyl)-4-methyl-N-(piperidin-1-yl)-1H-pyrazole-3-carboxamide); SKF 9635 (1-(beta-[3[(4-methoxy-phenyl)propoxyl]-4-methoxyphenyethyl)-1H-imidazole hydrochloride); and other compounds. As used herein, the terms "NSC antagonist" and "NSC antagonists" include blockers of the TRPM4 channel, including those listed above. In embodiments of the invention, the blockade of the TRPM4 channels by NSC antagonists is effective to reduce the amount of neuronal cell death associated with dementia, such as AD. In embodiments of the invention, the blockade of TRPM4 channels by NSC antagonists is effective to prevent from occurring, delay, or ameliorate neuronal cell death associated with dementia, such as AD.

Thus, the present invention provides compounds, pharmaceutical compositions, methods of treatment, and kits comprising NSC antagonists for treating dementia, such as AD. Such treatment may provide preventative treatment for persons not presently suffering from dementia, such as AD, or for persons thought to be at risk for developing dementia, such as AD, and may provide therapeutic treatment for persons suffering from dementia, such as AD, or from a dementing condition related to AD.

In one example, a person at risk for developing AD would take a NSC antagonist such as glibenclamide in order to prevent or delay the onset of the disease. The drug may be taken orally or transdermally, although it will be understood that any suitable mode of delivery (e.g. subcutaneously, intravenously (IV), intramuscularly, etc.) may be used in the practice of the invention.

In another example, a person developing or having developed AD would take a NSC antagonist such as glibenclamide in order to treat the disease. The drug may be administered orally, topically (e.g., via transdermal patch, or via ointment) but any suitable mode of delivery (e.g. subcutaneously, intravenously (IV), intramuscularly, etc.) may be used in the practice of the invention.

In another example, a person having developed AD may take a NSC antagonist such as glibenclamide in order to treat the disease and signs and symptoms of AD would be monitored during treatment. The drug dosage may be adjusted upwards or downwards depending on clinical response to the drug. The drug may be administered orally or topically (e.g., via transdermal patch or via ointment), but any suitable mode of delivery (e.g. subcutaneously, IV, intramuscularly, etc.) may be used in the practice of the invention.

In another example, a person developing or having developed AD and who has concurrent diabetes may take a NSC antagonist such as glibenclamide in order to treat both the AD and diabetes. The drug may be administered orally or topically (e.g. via transdermal patch, or ointment), but any suitable mode of delivery (e.g. subcutaneously, intravenously (IV), intramuscularly, etc.) may be used in the practice of the invention. This dosage would need to be high enough to cause therapeutic effect for both AD and diabetes.

The dose may be low enough to cause therapeutic effect without causing hypoglycemia, although higher doses could be used if co-treated with an agent that would prevent hypoglycemia such as glucose or glucagon. Given this, while doses of 2.5 mg to 20 mg per day would be permissible, lower doses in the range 0.01 mg/day through to 2.5 mg per day would be preferable. Higher doses might be useful as "rescue treatments", or at the beginning of treatment, or intermittently to speed recovery.

Administration of NSC antagonists for ameliorating, treating, delaying, or preventing dementia, such as AD, includes administration of a single NSC antagonist; administration of two, or of more than two, NSC antagonists;

administration of one or more NSC antagonists with other drugs, where such other drugs may include drugs used to ameliorate, treat, delay, or prevent dementia such as AD; administration of one or more NSC antagonists with other drugs, where such other drugs may include drugs used to correct or stabilize blood glucose levels; and other forms of administration in conjunction with other drugs or treatments.

In embodiments in which administration of NSC antagonists for ameliorating, treating, delaying, or preventing dementia, such as AD, includes the administration of more than one NSC antagonist, suitable combinations of NSC antagonists may be provided where a) at least one NSC antagonist compound is selected from: glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, and phytoestrogens; and b) at least one NSC antagonist compound is selected from: pinkolant, flufenamic acid, mefanamic acid, niflumic acid, rimonabant, SKF 9635.

A NSC antagonist, such as, e.g., glibenclamide, may be administered in conjunction (either separately or together) with other compounds useful for treating AD or for ameliorating the symptoms of AD, including, e.g., drugs such as memantine (Namenda®; 1-amino-3,5-dimethyl-adamantane), donepezil (Aricept®; 2-[(1-benzyl-4-piperidyl)methyl]-5,6-dimethoxy-2,3-dihydroinden-1-one), galantamine (Nivalin (4aS,6R,8aS)-4a,5,9,10,11,12- hexahydro-3-methoxy-11-methyl-6H-benzofuro[3a,3,2-ef] [2]benzazepin-6-ol), rivastigmine (Exelon®; (S)-N-Ethyl-N-methyl-3-[1-(dimethylamino)ethy]-phenyl carbamate hydrogen-(2R,3R)-tartrate), tacrine (Cognex®; 1,2,34-tetrahydroacridin-9-amine); or other drug or drugs useful in the treatment, prevention, palliation, or amelioration of dementia, such as AD.

The length of treatment may extend for days, months or for years, and may comprise treatment with a NSC antagonist, or may comprise co-treatment with a SUR1 antagonist and with other drugs. In embodiments with other drugs, such other drugs may be drugs used in treating dementia. In preferred embodiments with other drugs, such other drugs are drugs used in treating AD. Suitable dosing regimens include single doses per day and include multiple times per day, daily, or less frequent doses. Where a transdermal patch is used to administer the NSC antagonist, or combination of drugs including a NSC antagonist, the dosing regimen may include placement of the patch at a suitable place on the skin of a subject and allowing the patch to remain in that position for a day, for multiple days, or for a week or multiple weeks, or for a month, or for two or more months.

Administration

The manner in which the compounds are administered can vary. The compounds can be administered topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro-ventricularly; or transdermally (e.g., using a transdermal patch). Although it is possible to administer the compounds in the form of a hulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time-release capsule. As another example, the compounds can be delivered transdermally using the types of patch technologies available from Novartis and Alza Corporation (now part of Johnson and Johnson). The administration of the pharmaceutical compositions of the present invention can be intermittent, or at a gradual, continuous, constant or controlled rate. In addition, the time of day and the number of times per day that the pharmaceutical formulation is administered can vary. Administration preferably is such that the active ingredients of the pharmaceutical formulation interact with receptor sites within the body of the subject that effect the functioning of the central nervous system (CNS). More specifically, in treating a CNS disorder administration preferably is such so as to optimize the effect upon those relevant receptor subtypes which have an effect upon the functioning of the CNS, while minimizing the effects upon muscle-type receptor subtypes. This may include the use of slow release capsules and pills to provide blood plasma levels of the agent that are substantially constant over time, or relatively less varying over time than would be the case with other modes of administration, rather than peaks and troughs associated with fast and regular-release capsules and pills. Other suitable methods for administering the compounds of the present invention are described in U.S. Pat. No. 5,604,231 to Smith et al.

Typical dosages for systemic administration of NSC antagonists may range from about 0.1 to about 1000 milligrams per kg weight of subject per administration. A typical dosage may be one 0.4-3000 mg tablet taken once a day, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release (see, e.g., osmotic drug delivery advice as shown, e.g., in U.S. Pat. No. 5,312,390; slow-release compositions as discussed, e.g., in U.S. Pat. No. 5,411,737).

Sulfonylurea Receptor 1 Antagonists are NSC Antagonists

Sulfonylureas and compounds that act at, and antagonize the activation or activity of, sulfonylurea receptors such as SUR1, are useful as NSC antagonists. Glibenclamide is an exemplary NSC antagonist, and is named herein as an example of one of the NSC antagonists that are suitable for the practice of the embodiments of the invention disclosed herein. Glibenclamide is also known as glybenclamide, glyburide, glybenzcyclamide, and by other names. The chemical name (IUPAC name) of glibenclamide is 5-chloro-N-[2-[4-(cyclohexylcarbamoylsulfamoyl) phenyl]ethyl]-2-methoxy-benzamide. Equivalent chemical names for glibenclamide include, e.g., 5-chloro-N-[2-[-4-[[[cyclohexylamino)carbonyl]amino]sulfony]phenyl]ethyl]-2-methoxy-benzamide (as reported in the *Merck Index* (12$^{th}$ Edition, Merck Research Laboratories, 1996, page 762), and 1[p-2[5-chloro-O-anisamido)ethyl]phenyl]sulfonyl]-3-cyclohexyl-3-urea.

It will be understood that any NSC antagonist is suitable for the practice of the embodiments of the invention disclosed herein, and that naming glibenclamide is not meant to be limiting. Other suitable NSC antagonists include, in addition to, glibenclamide: glibenciamide's active metabolites; such as (for example) 4-trans-hydroxy-glibenclamide and 3-cis-hydroxy-glibenclamide; tolbutamide (orinase®; 3-butyl-1-(4-methylphenyl)sulfonyl-urea); chlorpropamide (N-(4-chlorophenyl)sulfonylmethanamide; also given as 1-[[(p-chlorophenyl)sulfonyl]-3-propylurea); glipizide (1-cyclohexyl-3[[p-[2(5-methylpyrazine carboxamido) ethyl]phenyl]sulfonyl]urea); or tolazamide(benzenesulfonamide-N-[[(hexahydro-1H-azepin-1yl)amino ] carbonyl]-4-methyl), repaglinide, nateglinide (N-trans-4-isopropylcyclohexanecarbonyl)-D-phenylalanine), meglitinide, midaglizole, tolazamide, gliquidone, LY397364, LY389382, glyclazide, glimepiride, estrogen, estrogen related-compounds (estradiol, estrone, estriol, genistein, non-steroidal estrogen (e.g., diethystilbestrol), phytoestrogen (e.g., coumestrol), zearalenone, etc.), and combinations thereof. Examples of suitable NSC antagonists further include, but are not limited to, compounds known to inhibit or block $K_{ATP}$ channels (which include, without limitation, tolbutamide, glibenclamide, and other compounds named above, as well as MgADP, and other compounds).

NSC antagonists include compounds that block or reduce the physiological activity of the TRPM4 channel. NSC antagonists which are blockers of the TRPM4 channel include pinkolant ((R,S)-(3,4-dihydro-6,7-dimethoxy-isoquinoline-1-yl)-2-phenyl-N,N-di[2-(2,3,4-trimethoxyphenyl)ethyl]-acetamide)); fenamates, including flufenamic acid, mefanamic acid, and niflumic acid; rimonabant (SR141716A; (5-(4-Chlorophenyl)-1-(2,4-dichloro-phenyl)-4-methyl-N-(piperidin-1-yl)-1H-pyrazole-3-carboxamide); SKF 9635 (1-(beta-[3[(4-methoxy-phenyl)propoxyl]-4-methoxyphenyethyl)-1H-imidazole hydrochloride); and other compounds.

Dose Determinations

Any suitable medicament, pharmaceutical formulation, and dosage form may be used in the practice of the invention. A suitable medicament, pharmaceutical formulation, and dosage form is effective to deliver or provide a therapeutically effective amount of the drug or drug combination to the patient. For example, suitable pharmaceutical dosage forms include a pill, a tablet, an oral formulation, a gel, an ointment, a transdermal patch, an intravenous solution, a formulation for intramuscular administration, a formulation for peritoneal administration, and a formulation for subcutaneous administration. Pharmaceutical dosage forms may be designed to provide stable plasma levels for extended periods of time. Thus, suitable. pharmaceutical dosage forms include forms for injection; oral forms; topical forms; tablets, pills, capsules, gels, and so forth; sustained release forms, enteric-coated forms, implantable forms including depot and pump forms, and other pharmaceutical forms.

By a "therapeutically effective amount" or simply "effective amount" of an active compound, such as glibenclamide or tolbutamide, is meant a sufficient amount of the compound to treat, prevent or alleviate AD or a condition related to AD. It will be understood, however, that the total daily usage of the active compounds and compositions of the present invention will be decided by the attending physician within the scope of sound medical judgment. The specific therapeutically effective dose level for any particular patient will depend upon a variety of factors including the disorder being treated and the severity of the disease; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in. the medical arts.

Toxicity and therapeutic efficacy of such compounds can be determined by standard pharmaceutical procedures in cell assays or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell based assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The total daily dose of the active compounds of the present invention administered to a subject in single or in divided doses can be in amounts, for example, from 0.01 to 25 mg or more usually from 0.1 to 15 mg. It will be understood that dosages will vary between the different NSC antagonists. However, in general, in embodiments, dosages may be between about 0.4 mg to about 3000 mg. In preferred embodiments, for example, glibenclamide dosages may be between about 0.4 mg to about 10 mg. Single dose compositions may contain such amounts or submuitipies thereof to make up the daily dose. In general, treatment regimens according to the present invention comprise administration to a human or other mammal in need of such treatment from about 0.01 mg to about 5 mg per day, or up to about 1000 mg of the active substance(s) of this invention per day in multiple doses or in a single dose of from 0.01 mg, 0.1 mg, 1 mg, 2.5 mg, 5 mg, 10 mg, 100 mg, 500 mg or 1000 mg.

An effective amount of a NSC antagonist or related-compounds thereof as a treatment varies depending upon the subject that is treated and the particular mode of administration. In one embodiment of the invention the dose range of the NSC antagonist or related-compounds thereof will be about 0.01 µg/kg body weight to about 20,000 µg/kg body weight. All concentrations and treatment levels are expressed as "body weight" or simply "kg" in this application are also considered to cover the analogous "total body weight" concentrations. However, those of skill will recognize the utility of a variety of dosage range, for example, 0.01 µg/kg body weight to 20,000 µg/kg body weight, 0.02 µg/kg body weight to 15,000 µg/kg body weight, 0.03 µg/kg body weight to 10,000 µg/kg body weight, 0.04 µg/kg body weight to 5,000 µg/kg body weight, 0.05 µg/kg body weight to 2,500 µg/kg body weight, 0.06 µg/kg body weight to 1,000 µg/kg body weight, 0.07 µg/kg body weight to 500 µg/kg body weight, 0.08 µg/kg body weight to 400 µg/kg body weight, 0.09 µg/kg body weight to 200 µg/kg body weight or 0.1 µg/kg body weight to 100 µg/kg body weight. Further, those of skill will recognize that a variety of different dosage levels will be of use, for example, 0.0001

µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/kg, 15.0 µg/kg, 30.0 µg/kg, 50 µg/kg, 75 µg/kg, 80 µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 mg/kg, 5 mg/kg, 10 mg/kg, 12 mg/kg, 15 mg/kg, 20 mg/kg, and/or 30 mg/kg. Of course, all of these dosages are exemplary, and any dosage in-between these points is also expected to be of use in the invention. Any of the above dosage ranges or dosage levels may be employed for a NSC antagonist or related-compounds thereof.

For example, in certain embodiments, the amount of the NSC antagonist administered to the subject is in the range of about 0.0001 µg/kg/day to about 20 mg/kg/day, about 0.01 µg/kg/day to about 100 µg/kg/day, or about 100 µg/kg/day to about 20 mg/kg/day. Still further, the NSC antagonist may be administered to the subject in the from of a treatment in which the treatment may comprise the amount of the NSC antagonist or the dose of the NSC antagonist that is administered per day (1, 2, 3, 4, etc.), week (1, 2, 3, 4, 5, etc.), month (1, 2, 3, 4, 5, etc.), etc. Treatments may be administered such that the amount of NSC antagonist administered to the subject is in the range of about 0.0001 µg/kg/treatment to about 20 mg/kg/treatment, about 0.01 µg/kg/treatment to about 100 µg/kg/treatment, or about 100 µg/kg/treatment to about 20 mg/kg/treatment, In embodiments, a NSC antagonist dosage may be between about 0.01 mg to about 15 mg. In preferred embodiments, a dosage may be between about 0.4 mg to about 10 mg per day. For example, a suitable daily dose of glibenclamide may be less than about 10 mg per day; in particular embodiments, a suitable daily dose of glibenclamide may be about 0.4 mg/day to about 10 mg/day, or about 4-9 mg per day, or about 5-8 mg per day, or other amount as determined by the weight, age, sex, liver and kidney status, or other characteristic of the patient. Dosage forms, such as pills including a NSC antagonist as an active ingredient, along with other ingredients such as pharmaceutically acceptable excipients, may include, for example, about 10 mg, or about 5 mg, or about 2.5 mg, or about 1 mg, or about 0.5 mg, or about 0.1 mg of glibenclamide.

It is believed that suitable glibenclamide doses useful for treating AD will typically result in blood plasma concentrations of about 2-6 ng/ml or higher. Thus, in embodiments, treatments will result in suitable blood plasma concentrations of about 5 ng/ml, or of about 4 ng/ml, or of about 3 ng/ml, or of about 2 ng/ml, or of about 1 ng/ml, or higher blood plasma concentrations.

In alternative embodiments, for example, a suitable dose of oral or intravenous (IV) glibenclamide for the treatment of AD may be about 0.01 mg to about 10 mg per day; a suitable dose of oral or IV tolbutamide for the treatment of AD may be about to 0.001 mg to about 3,000 mg per day; a suitable dose of oral gliclazide for the treatment of AD may be about 0.1 mg to about 100 mg per day;

In certain situations, it may be important to maintain a fairly low dose of the active agent in the blood stream of the patient. Such a fairly low dose may include a dose that is less than its use in other indications. For example, the typical anti-diabetic dose of oral glibenclamide is about 2.5 mg to about 15 mg per day; the typical anti-diabetic dose of oral or IV tolbutamide is about to 500 mg to about 3000 mg per day; the typical anti-diabetic dose for oral gliclazide is about 30 mg to about 120 trig per day; however, in embodiments, smaller doses may be used in treatment of AD. Where smaller doses are used, such smaller doses may be, for example, less than about 2.5 mg/day of glibenclamide, less than about 500 mg per day of tolbutamide, less than about 30 mg per day of oral gliclazide, or other doses. Such smaller doses may be used, for example, where multiple doses are administered during the course of a single day, effective reduce the variability in the plasma levels of the drug over time.

In particular, it is believed that preferred dosages of glibenclamide for use according to the present invention provide between about 0.4 mg to about 10 mg glibenclamide per day; preferred dosages of tolbutamide for use according to the present invention provide between about 50 mg to about 1000 mg tolbutamide per day; and preferred dosages of gliclazide for use according to the present invention provide between about 5 mg to about 20 mg gliclazamide per day.

In certain situations, it may be important to maintain a fairly high dose of tine active agent in the blood stream of the patient, particularly early in the treatment. Such a fairly high dose may include a dose that is several times greater than its use in other indications. For example, the typical anti-diabetic close of oral glibenclamide is about 2.5 mg to about 15 mg per day; the typical anti-diabetic dose of oral tolbutamide is about to 0.5 gm to about 3.0 gm per day; the typical anti-diabetic dose for oral gliclazide is about 30 mg to about 120 mg per day; however, larger doses may be required in some cases.

For example, in one embodiment of the present invention directed to a method of preventing or treating AD in a subject by administering to the subject a formulation containing an effective amount of a NSC antagonist and a pharmaceutically acceptable carrier; such formulations may contain, for example, from about 0.01 to about 3000 milligrams of tolbutamide or from about 0.05 to about 50 milligrams of glibenclarnide, In regards to oral glibenclamide for AD in non diabetics, doses may be in the range 0.1 mg/day to 10 mg/day or even as high as 15-20 mg/day, and would be divided into low dose pills given as few as 1 doses a day, and as many as 4-6 doses. Dose regimens are designed so as to maintain the plasma concentrations of glibenclamide, or of any other NSC antagonist, steady over time, and so as to, as much as possible, avoid or minimize large peaks and valleys or plasma concentration over time. Administration more than twice a day is often associated with low compliance, thus it is considered that in practice maximal numbers or doses per day may be about 4-6 doses per day.

A preferred method of administration includes transdermal administration of NSC antagonist, such as by use of a transdermal patch. For example, transdermal glibenclamide patches as presently used for treatment of diabetes may be used in the methods disclosed herein, as adapted to provide proper dosage levels of NSC antagonist, such as glibenclamide, for treatment, palliation, amelioration, or prevention of AD.

A NSC antagonist may be administered intravenously. For example, where glibenclamide is administered to a patient for the treatment of AL), smaller amounts of glibenclamide may be required to obtain a blood plasma level of about 6 ng/ml, so that, for example, as little as about 0.5 mg/day glibenclamide may be administered intravenously.

A suitable amount of NSC antagonist may also be an amount that maintains a reasonable level of blood glucose in the patient, for example, the amount of the antagonist maintains a blood glucose level of at least 60 mg/dl. More preferably, the blood glucose level is maintained in the range of about 60 mg/dl to about 150 mg/dl. Thus, the amount of NSC antagonist may be provided so as to prevents the subject from becoming hypoglycemic. If glucose levels are not normal, then one of skill in the art would administer either insulin or glucose, depending upon if the patient is hypoglycemic or hyperglycemic.

Glucose may be administered with a NSC antagonist in embodiments of the present methods of preventing or treating AD in a subject. Thus, in embodiments of the methods disclosed herein, the methods include co-administration of a NSC antagonist with glucose, or with a related carbohydrate, or both, effective to maintain appropriate levels of serum glucose. Appropriate serum levels of blood glucose are within the range of about 60 mg/dl to about 150 mg/dl. Thus, glucose, or a related carbohydrate, or both, may be administered, alone or in combination, to maintain the serum glucose within this range or within.

A NSC antagonist such as glibenclamide may be administered in conjunction (either separately or together) with drugs used for treating AD patients such as, e.g., memantine (Namenda®; 1-amino-3,5-dimethyl-adamantane), donepezil (Aricept®; 2-[(1-benzyl-4-piperidyl)methyl]-5,6-dimethoxy-2,3-dihydroinden-1-one), galantamine (Nivalin®; (4aS,6R,8aS)-4a,5,9,10,11,12- hexahydro-3-methoxy-11-methyl-6H-benzofuro[3a,3,2-ef] [2]benzazepin-6-ol), rivastigmine (Exelon®; (S)-N-Ethyl-N-methyl-3-[1-(dimethylamino)ethyl]-phenyl carbamate hydrogen-(2R,3R)-tartrate), or other drugs useful in the treatment, prevention, palliation, or amelioration of AD. Such drugs used for treating AD patients are termed "AD drugs." Administration of NSC antagonists in conjunction with AD drugs includes, without limitation: simultaneous or concomitant administration of a NSC antagonist with an AD drug; administration of a NSC antagonist followed by administration of an AD drug; and administration of an AD drug followed by administration of a NSC antagonist. Simultaneous or concomitant administration includes administration of both drugs, or of both types of drugs, within a few minutes or within a few tens of minutes of each other.

Accordingly, compositions and pharmaceutical formulations of the present invention include combined dosage forms including as active ingredients a NSC antagonist and another drug. The other drug is preferably a drug that is used in the treatment of AD, or a drug that is useful in the treatment of AD. In embodiments, the other drug may be memantine, or donepezil, or galantamine, or rivastigmine, or tacrine, or any combination thereof. Combined pills having features of the invention include pills providing suitable amounts of NSC antagonist, as discussed above. Thus, for example, where the NSC antagonist is glibenclamide, a combined dosage form may include in a single pill, tablet, capsule, or other dosage form, for example, glibenciamide with memantine; glibenclamide with donepezil; glibenclamide with galantamine; glibenclamide with rivastigmine; or glibenclamide with tacrine. Similarly, where the NSC antagonist is tolbutamide, a combined dosage form may include in a single pill, tablet, capsule, or other dosage form, for example, tolbutamide with memantine; tolbutamide with donepezil; glibenclarnide with galantamine; tolbutamide with rivastigmine; or tolbutamide with tacrine. It will be understood that a combined dosage form may include in a single pill, tablet, capsule, or other dosage form having features of the invention any combination of a NSC antagonist and a drug used in, or useful for, treating AD, and may include more than one NSC antagonist; more than one drug used in, or useful for, treating AD; and may include more than one of both a NSC antagonist and more than one drug used in, or useful for, treating AD.

For example, a single pill, tablet, capsule, or other dosage form having features of the invention may include about 0.4-5 mg glibenclamide with about 5-10 mg memantine. Other examples, listed to provide examples but not to limit the single pill, tablet, capsule, or other dosage forms disclosed herein, include about 1-5 mg glibenciamide with about 5-10 mg donepezil; about 1-5 mg glibenciamide with about 1-5 mg rivastigmine; about 1-5 mg glibenciamide with about 4-12 mg galantamine; about 1-5 mg glibenclamide with about 10-40 mg tacrine; and other combinations.

A transdermal patch having features of the invention may combine active ingredients a NSC antagonist and another drug. The other drug is preferably a drug that is used in the treatment of AD, or a drug that is useful in the treatment of AD. In embodiments, the other drug may be memantine, or donepezil, or galantamine, or rivastigmine, or tacrine, or any combination thereof. Combined transdermal patches having features of the invention include pills providing suitable amounts of NSC antagonist, as discussed above. Thus, for example, where the NSC antagonist is glibenclamide, a combined transdermal patch may include, for example, glibenclamide with memantine; glibenclamide with donepezil; glibenclamide with galantamine; glibenclamide with rivastigmine; or glibenclamide with tacrine. Similarly, where the NSC antagonist is tolbutamide, a combined transdermal patch may include, for example, tolbutamide with memantine; tolbutamide with donepezil; glibenclamide with galantamine; tolbutamide with rivastigmine; or tolbutamide with tacrine. It will be understood that a transdermal patch having features of the invention may include any combination of a NSC antagonist and a drug used in, or useful for, treating AD, and may include more than one NSC antagonist; more than one drug used in, or useful for, treating AD; and may include more than one of both a NSC antagonist and more than one drug used in, or useful for, treating AD.

Methods

Applicants disclose herein that the onset of dementia may be prevented or delayed, and that dementia may be treated, or its symptoms relieved, by administration of an effective amount of a NSC antagonist to a patient at risk of developing dementia, or suffering from the onset of dementia, or suffering from dementia. The dementia may be AD. The NSC antagonist may be, for example, glibenclamide, glibenclamide's active metabolites (e.g., 4-trans-hydroxy-glibenclamide and 3-cis-hydroxy-glibenclamide), tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, or a combination thereof. In embodiments, the NSC antagonist is selected from glibenclamide, tolbutamide, chlorpropamide, tolazamide, repaglinide, nateglinide, meglitinide, midaglizole, tolazamide, gliquidone, LY397364, LY389382, glyclazide, glimepiride, and combinations thereof.

Applicants further disclose herein that the onset of dementia may be prevented or delayed, and that dementia may be treated, or its symptoms relieved, by administration of an effective amount of a NSC antagonist in combination with an other drug that is used to treat dementia, to a patient at risk of developing dementia, or suffering from the onset of dementia, or suffering from dementia. The dementia may be AD. The NSC antagonist may be glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, or a combination thereof. In embodiments, the NSC antagonist is selected from glibenclamide, tolbutarnide, chlorpropamide, tolazamide, repaglinide, nateglinide, meglitinide, midaglizole, tolazamide, gliquidone, LY397364, LY389382, glyclazide, glimepiride, and combinations thereof. The other drug that is used to treat dementia may be, for example, selected from memantine, donepezil, galantamine, rivastigmine, tacrine, and combinations thereof.

In further embodiments of the methods disclosed herein, a substance is administered to the patient effective to maintain blood plasma glucose levels within an acceptable physiological concentration range. In some embodiments, the substance is glucose. In some embodiments, the substance is glucagon. In some embodiments, both glucose and glucagon are administered.

In further embodiments of the methods disclosed herein, blood plasma glucose levels are monitored. Blood glucose level monitoring may be performed before administration of a NSC antagonist, or before administration of a NSC antagonist with an other dementia drug, or before administration of a substance effective to maintain blood plasma glucose levels within an acceptable physiological range, or before administration of a NSC antagonist with an other dementia drug and with a substance effective to maintain blood plasma glucose levels within an acceptable physiological range.

In further embodiments, blood glucose level monitoring may be performed during administration of a NSC antagonist, or during administration of a NSC antagonist with an other dementia drug, or during administration of a substance effective to maintain blood plasma glucose levels within an acceptable physiological range, or during administration of a NSC antagonist with an other dementia drug and with a substance effective to maintain blood plasma glucose levels within an acceptable physiological range.

Blood glucose level monitoring may be performed after administration of a NSC antagonist, or after administration of a NSC antagonist with an other dementia drug, or after administration of a substance effective to maintain blood plasma glucose levels within an acceptable physiological range, or after administration of a NSC antagonist with an other dementia drug and with a substance effective to maintain blood plasma glucose levels within an acceptable physiological range.

In further embodiments, blood glucose level monitoring may be performed at any time with respect to the administration of a NSC antagonist, or the administration of a NSC antagonist with an other dementia drug, or the administration of a substance effective to maintain blood plasma glucose levels within an acceptable physiological range, or the administration of a NSC antagonist with an other dementia drug and with a substance effective to maintain blood plasma glucose levels within an acceptable physiological range.

Blood plasma concentrations of glibenclamide of as low as 2-6 ng/ml are effective to statistically significant reductions in blood plasma glucose levels in sonic patients. Thus in an embodiment, blood plasma levels of glibenclamide are maintained at about 2-6 ng/ml or more. In further embodiments, glucose is provided in order to maintain blood glucose levels within the desirable range (typically above about 60 mg/dl, or between about 60 mg/dl to about 150 mg/dl). Glucose may be administered at the same time as the glibenclamide; may be administered at different times (e.g., before or after glibenclamide administration); and glucose may be administered by another route of administration (or separate pill) in order to keep blood plasma glucose levels within the desirable range. In embodiments of the methods of the invention, glucose levels may be monitored. For example, a glucose monitoring system may be used monitor glucose levels and to aid in determining the proper amounts of glucose to be administered in order to adjust glucose administration specifically for that particular patient. Such a glucose monitoring system may be one-time glucose monitoring system; may be an intermittent glucose monitoring system; and may be a continuous glucose monitoring system.

Formulations and Administration

The NSC antagonist compounds for use in the compositions, formulations, methods, and kits of the present invention may be administered alone or in combination or in concurrent therapy with other agents which affect the central or peripheral nervous system, particularly selected areas of the brain. Compositions and formulations suitable for the practice of the invention include pharmaceutical dosage forms that are suitable for administration by one or more of any suitable route of administration, and include a pill, a tablet, an oral formulation, an intravenous formulation, an intra-arterial formulation, an intramuscular formulation, a subcutaneous formulation, a peritoneal formulation, an inhalational formulation, a rectal formulation, a vaginal formulation, a topical formulation, a gel, an ointment, and a transdermal patch.

In compositions, formulations, methods and kits of the invention, NSC antagonist compounds can be incorporated into a pharmaceutically acceptable formulation for administration. Those of skill in the art can readily determine suitable dosage levels when the invention compounds are so used. In embodiments of the invention, compositions and formulations comprising at least one NSC antagonist compound, and a pharmaceutically acceptable carrier are contemplated.

As employed herein, the phrase "suitable dosage levels" refers to levels of compound sufficient to provide circulating concentrations high enough to prevent or treat dementia, such as AD, in a patient. In embodiments of the invention, such dosages are effective to block the $NC_{Ca\text{-}ATP}$ channel in vivo.

Pharmaceutical dosage forms include a NSC antagonists or a pharmaceutically acceptable salt, solvate, or solvate of a salt thereof, and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g.,. Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995), each of which is incorporated herein by reference for all purposes.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated. Such fluids are prepared with water for injection USP.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include: alcohol, e.g., 5% alcohol (e.g., in dextrose and water ("D/W") or D/W in normal saline solution ("NSS"), including in 5% dextrose and water ("D5/W"), or D5/W in NSS); synthetic amino acid such as Aminosyn, FreAmine, Travasol, e.g., 3.5 or 7; 8.5; 3.5, 5.5 or 8.5% respectively; ammonium chloride e.g., 2.14%; dextran 40, in NSS e.g., 10% or in D5/W e.g., 10%; dextran 70, in NSS e.g., 6% or in D5/W e.g., 6%; dextrose (glucose, D5/W) e.g., 2.5-50%; dextrose and sodium chloride e.g., 5-20% dextrose and 0,22-0.9% NaCl; lactated Ringer's (Hartmann's) e.g., NaCl 0.6%, KCl 0.03%, $CaCl_2$ 0.02%; lactate 0.3%; mannitol e.g., 5%, optionally in combination with dextrose e.g., 10% or NaCl e.g., 15 or 20%; multiple electrolyte solutions with varying combinations of electrolytes, dextrose, fructose, invert sugar Ringer's e.g., NaCl 0.86%, KCl 0.03%, $CaCl_2$ 0.033%; sodium bicarbonate e.g., 5%; sodium chloride e.g., 0.45, 0.9, 3, or 5%; sodium lactate e.g., ⅙ M; and sterile water for injection The pH of such IV fluids may vary, and. will typically be from 3.5 to 8 as known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed. oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric. coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate absorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal administration of the present invention may also comprise the use of a "patch". For example, the patch may supply one or more active substances at a predetermined rate and in a continuous manner over a fixed period of time. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. In addition, a patch may include penetration enhancers. Suitable penetration enhancers include glycerin, alcohols, alkyl methyl sulfoxides, pyrrolidones and luarocapram.

Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions, Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Therapeutic kits of the present invention are kits comprising an antagonist or a related-compound thereof Thus, the kit may comprise an NSC antagonist or related-compound thereof to block and/or inhibit the $NC_{Ca-ATP}$ channel or to block or inhibit a TRPM4 channel. Such kits will generally contain, in suitable container means, a pharmaceutically acceptable formulation of NSC antagonist or related-compound thereof; may contain, in suitable container means, a pharmaceutically acceptable formulation of an AD drug or related-compound thereof and may include a compound effective to raise or to maintain, at suitable levels, blood plasma glucose concentrations. The kit may have a single container means, and/or it may have distinct container means for each compound.

A pharmaceutically acceptable formulation is a composition, including at least one active ingredient, and including one or more other ingredients, such as, for example, diluents, solutions, buffers, carriers, excipients, binders, extenders, osmoticants, and other compounds and ingredients as are suitable for dissolving, storing, and/or delivering an active pharmaceutical agent.

Kits comprising pharmaceutical compositions and/or formulations suitable for preventing AD, or for treating AD, may include instructions for administration of the pharmaceutical compositions and/or formulations, and may include containers suitable for holding the pharmaceutical compositions and/or formulations. Such containers of such kits may be suitable for organizing pills, vials, or other unit dosage forms for daily, weekly or other dosage regimens.

Kits may comprise a pharmaceutically acceptable formulation of a NSC antagonist, and a pharmaceutically acceptable formulation of an AD drug. IN embodiments, a kit may comprise a pharmaceutically acceptable formulation of a NSC antagonist, a pharmaceutically acceptable formulation of an AD drug, and a pharmaceutically acceptable formulation of a compound effective to increase blood plasma glucose levels. A compound effective to increase blood plasma glucose levels may be, for example, glucagon, or glucose, or both, or other compound.

When the components of the kit are provided in one and/or more liquid solutions, the liquid solution is an aqueous solution, with a sterile aqueous solution being particularly preferred. The NSC antagonist or related-compounds thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

In addition to the NSC antagonist or related-compounds thereof, the kits may also include a second active ingredient. Examples of the second active ingredient include substances to prevent hypoglycemia (e.g., glucose, glucagon, glucose solutions such as 5% dextrose in water (D5W), and other substances), and steroids (e.g., methylprednisolone), etc. These second active ingredients may be combined in the same vial as the NSC antagonist or related-compounds thereof or they may be contained in a separate vial.

All patents and publications discussed herein are hereby incorporated by reference in their entireties.

EXAMPLES

The following exemplary descriptions illustrate ways to implement methods and treatments disclosed herein.

A 56-year old man with a family history of AD in his grandfather, father and elder sibling presents to a neurologist concerned about his risk of AD. Upon examination be is found to be cognitively normal, with no clinical signs of neurological disease. The patient is begun on a low dose of daily glibenclamide of 0.5 mg per day for transdermal administration, to be taken on a chronic basis as a prophylactic treatment.

A 56-year old man with a family history of AD in his grandfather, father and eider sibling presents to a neurologist concerned about his risk of AD. Upon examination be is found to be cognitively normal, with no clinical signs of neurological disease. The patient is begun on a low dose of daily glibenclamide of 0.5 mg per day for oral administration, to be taken on a chronic basis as a prophylactic treatment.

The daughter of an 83-year old female notices her mother exhibiting episodes of forgetfulness, and a situation in which the mother is unable to locate her car in a shopping center parking lot. The elderly patient is brought to a geriatrician, where mini-mental state examination reveals short-term memory loss and mild cognitive impairment. A diagnosis of AD is made as other causes are ruled out. The patient begins a course of daily glibenclamide of 1 mg per day administered via monthly depot intramuscular injection. Depot injection is chosen in order to optimize patient compliance. Neurological testing detects a stabilization of symptoms due to the treatment.

A 68-year old type 2 diabetic male presents to his family physician with complaints of forgetfulness and increasing confusion. He is being treated with metformin and diet controls for his Type 2 diabetes. The patient is diagnosed with AD upon referral to a geriatrician and upon clinical, laboratory and imaging investigations. The patient begins a daily dose of glibenclamide at 10 mg per day, and his daily metformin is ceased. The patient demonstrates stable blood glucose measurements and HbA1C levels, and the patient notes that his episodes of forgetfulness are waning with this treatment regimen.

The invention claimed is:

1. A container containing a composition suitable for intravenous administration, the composition comprising glibenclamide or a pharmaceutically acceptable salt thereof, mannitol, and a pharmaceutically acceptable carrier.

2. The container of claim 1, wherein the composition further comprises a compound effective to increase blood plasma glucose levels.

3. The container of claim 2, wherein said compound is glucose or glucagon.

4. The container of claim 1, wherein the composition further comprises dextrose.

5. The container of claim 1, wherein the composition comprises sterile water.

6. The container of claim 1, wherein. the container contains a single dose composition containing from 0.1 mg to 15 mg glibenclamide or a pharmaceutically acceptable salt thereof.

7. The container of claim 1, wherein the container contains a single dose composition containing from 0.4 mg to 10 mg glibenclamide or a pharmaceutically acceptable salt thereof.

8. The container of claim 1, wherein the container contains a single dose composition containing from 0.1 to 1 mg glibenclamide or a pharmaceutically acceptable salt thereof.

9. The container of claim 1, wherein the composition further comprises NaCl.

10. The container of claim 1, wherein the composition further comprises KCl.

11. The container of claim 1, wherein the composition further comprises $CaCl_2$.

12. The container of claim 1, wherein the composition further comprises lactate.

13. The container of claim 1, wherein the composition further comprises sodium bicarbonate.

14. The container of claim 1, wherein the composition further comprises an amino acid.

15. The container of claim 1, wherein the composition has a pH of from 3.5 to 8.

16. The container of claim 1, wherein the container is a syringe or a vial.

17. A container containing a composition suitable for intravenous administration, wherein the composition comprises about 1 mg glibenclamide or a pharmaceutically acceptable salt thereof, mannitol, and sterile water.

18. A method of making the container of claim 1, comprising miring glibenclamide, or a pharmaceutically acceptable salt thereof with mannitol and a pharmaceutically acceptable carrier to produce the composition, and filling the container with the composition.

19. The method of claim 18, wherein the container contains 0.4 mg to 10 mg glibenclamide or a pharmaceutically acceptable salt thereof.

20. The method of claim 18, wherein the pharmaceutically acceptable carrier comprises water.

* * * * *